United States Patent
Jou et al.

(10) Patent No.: US 9,452,058 B2
(45) Date of Patent: Sep. 27, 2016

(54) ARTIFICIAL IMPLANT FOR CARPOMETACARPAL JOINT

(71) Applicant: Fong-Chin Su, Tainan (TW)

(72) Inventors: I-Ming Jou, Tainan (TW); Wei-Jr Lin, Tainan (TW); Po-Ting Wu, Tainan (TW); Li-Chieh Kuo, Tainan (TW); Fong-Chin Su, Tainan (TW)

(73) Assignee: Fong-Chin Su, Tainan (TW)

( * ) Notice: Subject to any disclaimer, the term of this patent is extended or adjusted under 35 U.S.C. 154(b) by 0 days.

(21) Appl. No.: 14/752,577

(22) Filed: Jun. 26, 2015

(65) Prior Publication Data

US 2015/0297355 A1 Oct. 22, 2015

Related U.S. Application Data

(63) Continuation-in-part of application No. 14/057,737, filed on Oct. 18, 2013, now abandoned.

(30) Foreign Application Priority Data

Nov. 7, 2012 (TW) .............................. 101141387 A

(51) Int. Cl.
*A61F 2/42* (2006.01)
*A61B 17/06* (2006.01)
*A61F 2/30* (2006.01)

(52) U.S. Cl.
CPC ....... *A61F 2/4241* (2013.01); *A61B 17/06166* (2013.01); *A61F 2002/30257* (2013.01); *A61F 2002/30301* (2013.01); *A61F 2002/30578* (2013.01); *A61F 2002/30934* (2013.01); *A61F 2002/4258* (2013.01)

(58) Field of Classification Search
CPC ...... A61F 2/42; A61F 2/4225; A61F 2/4241; A61F 2002/4228; A61F 2002/423; A61F 2002/4233; A61F 2002/4235; A61F 2002/4238; A61F 2002/4243; A61F 2002/4246; A61F 2002/4248; A61F 2002/4251; A61F 2002/4253; A61F 2002/4256; A61F 2002/4258
See application file for complete search history.

(56) References Cited

U.S. PATENT DOCUMENTS

| | | | |
|---|---|---|---|
| 5,549,690 | A | 8/1996 | Hollister et al. |
| 8,066,777 | B2 | 11/2011 | Palmer et al. |
| 8,167,952 | B2 | 5/2012 | Graham et al. |

(Continued)

FOREIGN PATENT DOCUMENTS

| | | |
|---|---|---|
| CN | 2398987 Y | 10/2000 |
| CN | 102333501 A | 1/2012 |
| CN | 102764888 A | 11/2012 |

*Primary Examiner* — Brian Dukert
(74) *Attorney, Agent, or Firm* — Hauptman Ham, LLP

(57) ABSTRACT

An artificial implant for a carpometacarpal (CMC) joint used for replacing a CMC joint surface of the first metacarpal bone is provided and has: an insert portion having an inserting end for inserting into a bone marrow cavity exposed from an incision of the first metacarpal bone, and a front end; an articular replacement portion connected to the front end of the inserting portion and disposed outside the incision of the first metacarpal bone, and having an articular profile surface to replace the CMC joint surface of the first metacarpal bone; and an attached flange protruded from a peripheral of the articular replacement portion, attached to an outer bone surface of the first metacarpal bone adjacent to the incision, and having at least one suture hole, through which at least one suture passes for assisting to fix an abductor pollicis longus (APL) to the outer bone surface.

8 Claims, 7 Drawing Sheets

(56) References Cited

U.S. PATENT DOCUMENTS

| | | |
|---|---|---|
| 8,167,953 B2 | 5/2012 | Warburton |
| 8,641,770 B2 | 2/2014 | Scheker |
| 2008/0269908 A1 | 10/2008 | Warburton |
| 2009/0254190 A1 | 10/2009 | Gannoe |
| 2011/0087334 A1 | 4/2011 | Morton |
| 2011/0288550 A1 | 11/2011 | Orbay et al. |

ARTIFICIAL IMPLANT FOR CARPOMETACARPAL JOINT

CROSS REFERENCE TO RELATED APPLICATIONS

This application is a continuation in part application of U.S. patent application Ser. No. 14/057,737, filed on Oct. 18, 2013, the disclosure of which is incorporated herein by reference.

FIELD OF THE INVENTION

The present invention relates to an artificial implant, and more particularly to an artificial implant for a carpometacarpal (CMC) joint used with a surgical suture.

BACKGROUND OF THE INVENTION

Osteoarthritis is a disease that affects the joints. When intra-articular cartilage of the joints is damaged or worn, it causes osteoarthritis, and thus affects joint stiffness, pain and loss of function. Osteoarthritis commonly occurs in hip joint, knee joint, spinal joint and joints of the hand (such as palm and thumb joint). Among these, the carpometacarpal (CMC) joint arthritis is one of the most important issue in the degenerative arthritis disease of the upper limb. The CMC joint is located at the base portion of the thumb in anatomy, wherein a distal end of the CMC joint is a metacarpal bone, and a proximal end thereof is a trapezium close to the radial side. The CMC joint is the most activity joint of hand joints and can stretch, bend, adduct, abduct and rotate. Thus, once the CMC joint is degenerated, lesioned or wounded, it will cause great influence in daily life.

When the medicament or injection can't be effective to relieve pain and can't further deal with the degenerative arthritis of the CMC joint, the doctor generally advise the patient to be treated by a hand joint surgery. Further, the design of the artificial implant and the development of material fabrication thereof are continuously improved, so that artificial implants are applied to clinical use day by day. The injured CMC joint is replaced by arthroplasty surgery, and thus it not only reduces pain from arthritis, but also maintains the CMC joint activities and the behavior function of hand.

Briefly, the arthroplasty is a surgically method for reducing the pain from arthritis and restoring the joint function. The process of a traditional surgery for replacing an artificial CMC joint is firstly to crosscut a wound from the root of the thumb, then temporarily cut and remove the tendon of a abductor pollicis longus (APL) attached to the trapezium, open a joint capsule of the CMC joint, and abscise the damaged CMC joint surface at the proximal end of a first metacarpal to form an incision. Then, a portion of an implant is inserted into a bone marrow cavity of the first metacarpal from the incision at the proximal end of the first metacarpal. Thereafter, a surgical suture is used to reconstruct the APL tendon cut during the surgery, followed by suturing the wound.

However, during the surgery, it not only needs to temporarily cut the APL in the step of moving the APL tendon originally attached to the trapezium, but also needs to drill the first metacarpal to form two small holes for the surgical suture to pass therethrough, in order to arrange the surgical suture at both sides of the APL in advance. Thus, after the artificial implant is implanted into the bone marrow cavity, the APL tendon can be attached on the outer surface of the first metacarpal by surgical suturing. As mentioned above, the steps of cutting the APL tendon or drilling holes on the first metacarpal both are to destroy the tissue of the metacarpal or the tendon before reconstruction. In addition, the surgical suture arranged in advance is easily over-pushed into the bone marrow cavity by the artificial implant when the artificial implant is implanted into the bone marrow cavity. This causes the displacement of the surgical suture and thus it is difficult to carry out the precise positioning. Alternatively, the surgical suture arranged in advance may be destroyed by the artificial implant when the artificial implant is implanted into the bone marrow cavity, it's thus more difficult to process the reconstruction surgery for the APL tendon.

Therefore, it is necessary to provide an artificial implant for a carpometacarpal joint for solving the problems existing in the foregoing conventional technique.

SUMMARY OF THE INVENTION

A primary object of the present invention is to provide an artificial implant for a carpometacarpal (CMC) joint, wherein the artificial implant for the CMC joint has an attached flange to provide suture perforation, so as to omit the step of drilling holes on the first metacarpal. This facilitates the surgical suture to be fixed onto the artificial joint implant without destroying the tendon of the abductor pollicis longus (APL). Thus, it can simplify the surgical process to improve the surgery efficiency and increase the success rate of the arthroplasty surgery of the CMC joint.

To achieve the above object, the present invention provides an artificial implant for the carpometacarpal (CMC) joint, which is used for replacing a carpometacarpal joint surface of a first metacarpal bone and comprises:

an insert portion having an inserting end for inserting into a bone marrow cavity exposed from an incision of the first metacarpal bone, and a front end;

an articular replacement portion connected to the front end of the inserting portion and disposed outside the incision of the first metacarpal bone, and having an articular profile surface to replace the carpometacarpal joint surface of the first metacarpal bone; and an attached flange protruded from a peripheral of the articular replacement portion, configured to be attached to an outer bone surface of the first metacarpal bone adjacent to the incision, and having at least one suture hole.

wherein an interval is formed between the attached flange and the first metacarpal bone, and at least one suture passes through the interval and the suture hole, and the suture is knotted with an abductor pollicis longus for assisting to fix the abductor pollicis longus (APL) to the outer bone surface;

wherein the articular profile surface of the articular replacement portion is elliptical and includes a major axis and a minor axis, the major axis and the minor axis are crossed at a first intersection point, one end of the major axis close to the attached flange and the peripheral of the articular replacement portion are crossed at a second intersection point, a line is defined from the first intersection point to the attached flange, and an included angle defined between the line and the major axis is 1° to 45°, so that the attached flange is positioned and offset with respect to the second intersection point based on the articular profile surface; and wherein a ratio of the length of the major axis of the articular profile surface of the articular replacement portion and the length of the attached flange is 10:1 to 2:1.

In one embodiment of the present invention, the attached flange is integrally connected to the articular replacement portion through a tilting connection surface.

In one embodiment of the present invention, the suture hole is circular, oval or regular polygonal.

In one embodiment of the present invention, the insert portion, the articular replacement portion and the attached flange are integrated into one piece.

In one embodiment of the present invention, the material of the insert portion, the articular replacement portion and the attached flange are titanium, silica gel, zirconia or pyrocarbon.

In one embodiment of the present invention, the articular replacement portion and the attached flange are made of biocompatible metal or alloy and processed by powder injection molding and high-temperature sintering.

In one embodiment of the present invention, the articular profile surface is saddle-shaped, double parabolic concave discoid, single parabolic concave discoid, spherical, hemispherical, polygonal spherical or polygonal hemispherical.

In one embodiment of the present invention, the interval formed between the attached flange and the first metacarpal bone is equal to ½ to ⅖ of the thickness of the attached flange.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, and etc., are only directions by referring to the accompanying drawings, and thus the used directional terms are used to describe and understand the present invention, but the present invention is not limited thereto.

Figure 1A:
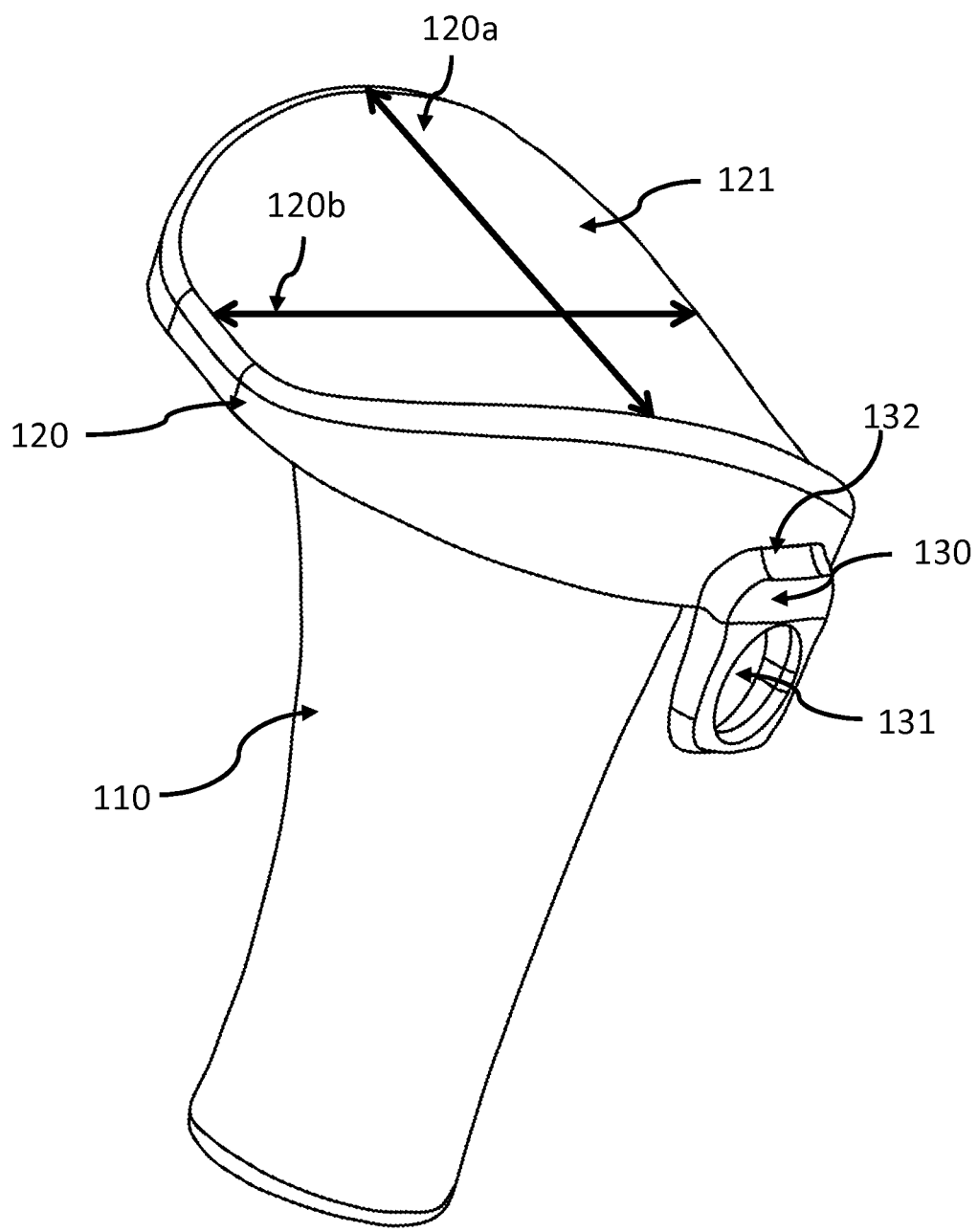
FIG. 1A is a perspective view of an artificial implant for a carpometacarpal joint according to a preferred embodiment of the present invention.

Referring now to FIG. 1A, an artificial implant 100 for a carpometacarpal (CMC) joint used for replacing a carpometacarpal joint articular surface of a first metacarpal bone according to a preferred embodiment of the present invention is illustrated. As shown, the artificial implant 100 for the carpometacarpal joint comprises: an insert portion 110, an articular replacement portion 120, and an attached flange 130, wherein the insert portion 110, the articular replacement portion 120 and the attached flange 130 are made of biocompatible metal or alloy, such as titanium, silica gel, zirconia or pyrocarbon. In this embodiment of the present invention, the insert portion 110, the articular replacement portion 120 and the attached flange 130 are made of biocompatible metal or alloy and processed by powder injection molding and high-temperature sintering; and the insert portion 110, the articular replacement portion 120 and the attached flange 130 are preferably integrated into one piece, but not limited thereto.

Figure 1B:
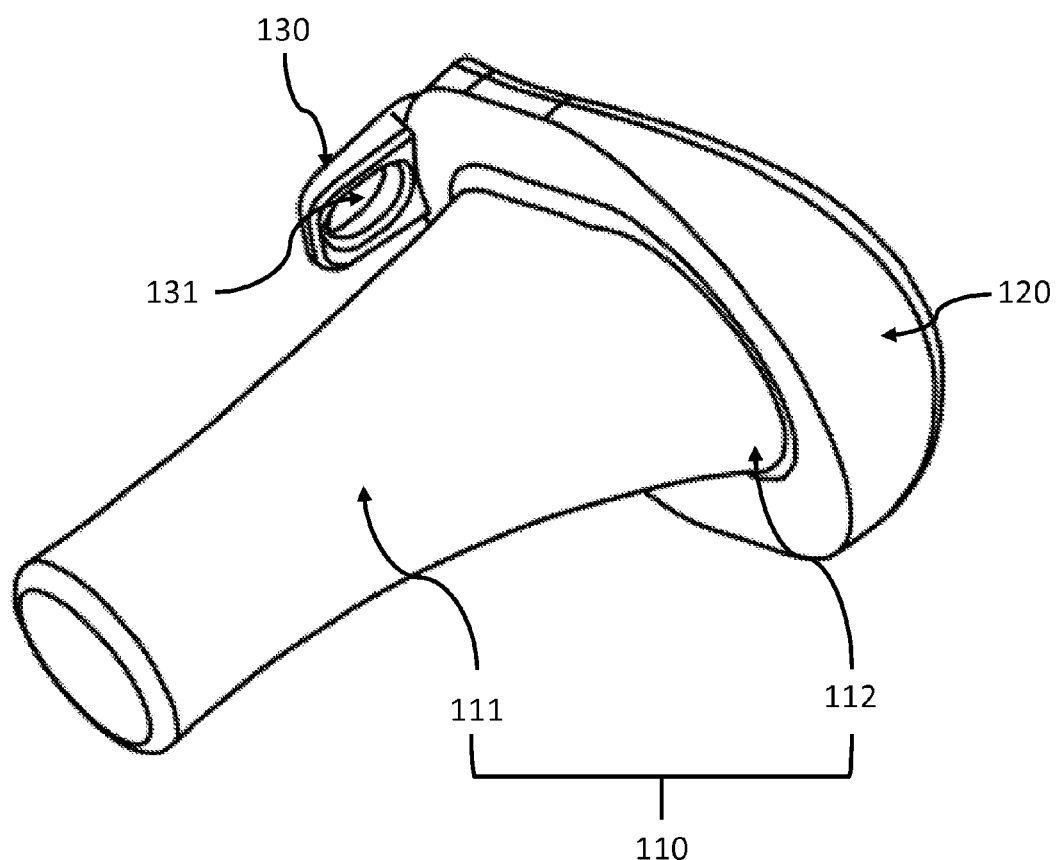
FIG. 1B is another perspective view of the artificial implant for the carpometacarpal joint according to the preferred embodiment of the present invention.

Referring to FIG. 1A and FIG. 1B, according to the artificial implant 100 for a carpometacarpal joint according to the preferred embodiment of the present invention, the insert portion 110 has an inserting end 111 and a front end 112, wherein the inserting end 111 is used for inserting into a bone marrow cavity exposed from an incision of the first metacarpal bone. The articular replacement portion 120 is connected to the front end 112 of the insert portion 110 and disposed outside the incision of the first metacarpal bone, and has an articular profile surface 121 to replace the carpometacarpal joint surface of the first metacarpal bone, where in the articular profile surface 121 can be saddle-shaped, double parabolic concave discoid, single parabolic concave discoid, spherical, hemispherical, polygonal spherical or polygonal hemispherical for being corresponding to a remote portion surface of a trapezium.

Figure 1C:
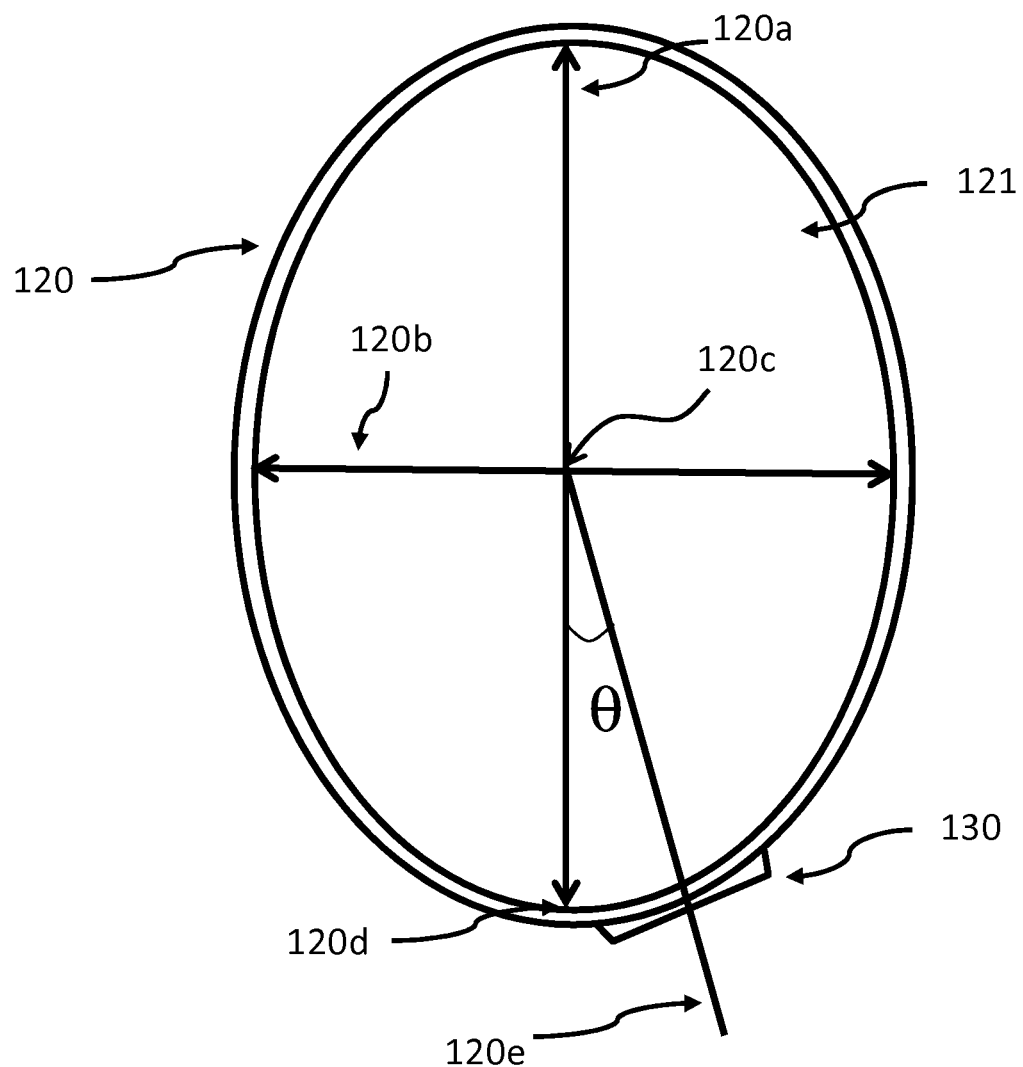
FIG. 1C is a top view of an articular profile surface of the artificial implant for the carpometacarpal joint according to the preferred embodiment of the present invention.

Referring still to FIG. 1A and FIG. 1C, in the preferred embodiment of the present invention, when the articular profile surface 121 of the articular replacement portion 120 is saddle-shaped or double parabolic concave discoid, the articular profile surface 121 includes a major axis 120a and a minor axis 120b, wherein the attached flange 130 is integrally connected to the articular replacement portion 120 through a tilting connection surface 132. The articular profile surface 121 is elliptical, and the attached flange 130 is protruded from the peripheral of the articular replacement portion 120. The major axis 120a and the minor axis 120b are crossed at a first intersection point 120c, while one end of the major axis 120a close to the attached flange 130 and the peripheral of the articular replacement portion 120 are crossed at a second intersection point 120d. A line 120e is defined from the first intersection point 120c to the attached flange 130, and an included angle θ defined between the line 120e and the major axis 120a is 1° to 45°, such as 2°, 4°, 6°, 8°, 10°, 12°, 15°, 18°, 20°, 25°, 30°, 35°, 36° or 40°. Thus, the attached flange 130 is positioned and offset with respect to the second intersection point 120d based on the top view of the articular profile surface 121. In more detail, the attached flange 130 is located at a position offsetting 1 to 45 degrees toward an outer side of a palm from an intersection point of the peripheral of the articular profile surface 121 and the major axis 120a of the articular profile surface 121, for being corresponding to the location of an attached portion of a tendon of a abductor pollicis longus (APL). In this embodiment of the present invention, a ratio of the length of the major axis 120a of the articular profile surface 121 of the articular replacement portion 120 and the length of the attached flange 130 is 10:1 to 2:1, such as 5:1, but not limited thereto.

In addition, in this embodiment of the present invention, the attached flange 130 is protruded from an peripheral of the articular replacement portion 120, and can be configured to be attached to an outer bone surface of the first metacarpal bone adjacent to the incision (i.e. corresponding to the location of the attached portion of the APL tendon), wherein the attached flange 130 has at least one suture hole 131, such as one, two, three or four, but not limited thereto. The suture hole 131 is circular, oval or regular polygonal, but not limited thereto. The diameter of the suture hole 131 is set in accordance with at least one times of the diameter of the suture. For example, the diameter of the suture hole 131 can be set to be two times, three times or more of the diameter of the suture. Moreover, the attached flange 130 is preferred integrally connected to the peripheral the articular replacement portion 120 through a tilting connection surface 132 for increasing the connection strength with the articular replacement portion 120.

Figure 2A:
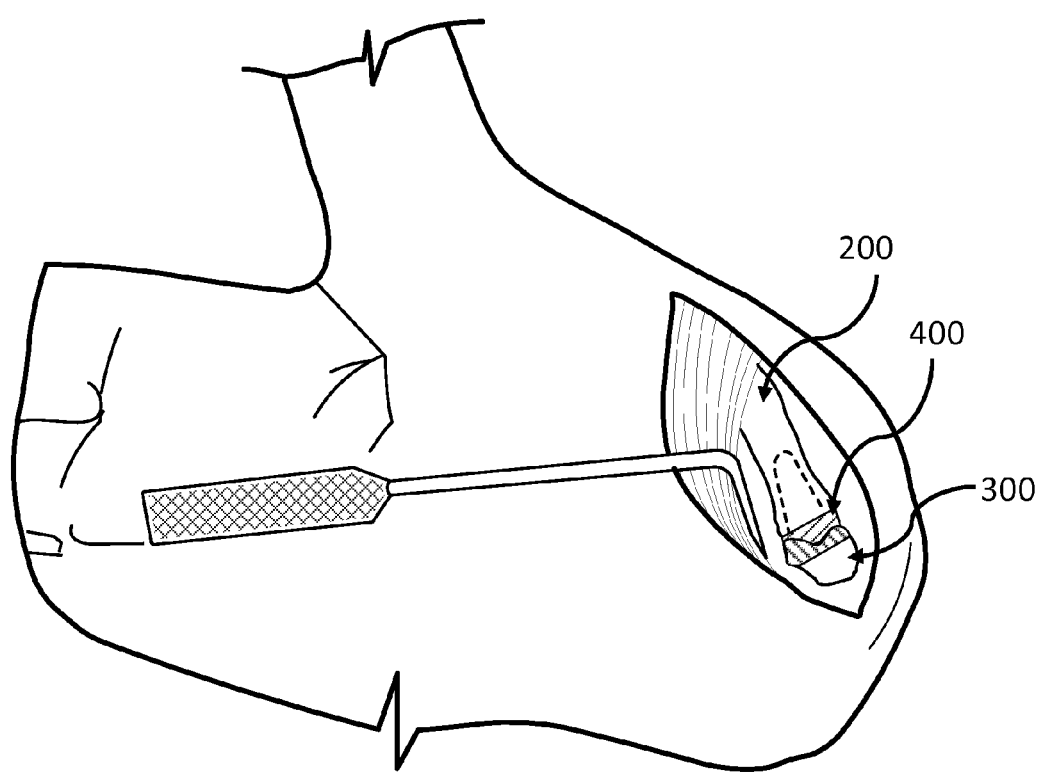
FIG. 2A is a schematic view of the artificial implant for the carpometacarpal joint according to the preferred embodiment of the present invention when cutting a wound from the skin of the root of the thumb.
Figure 2:
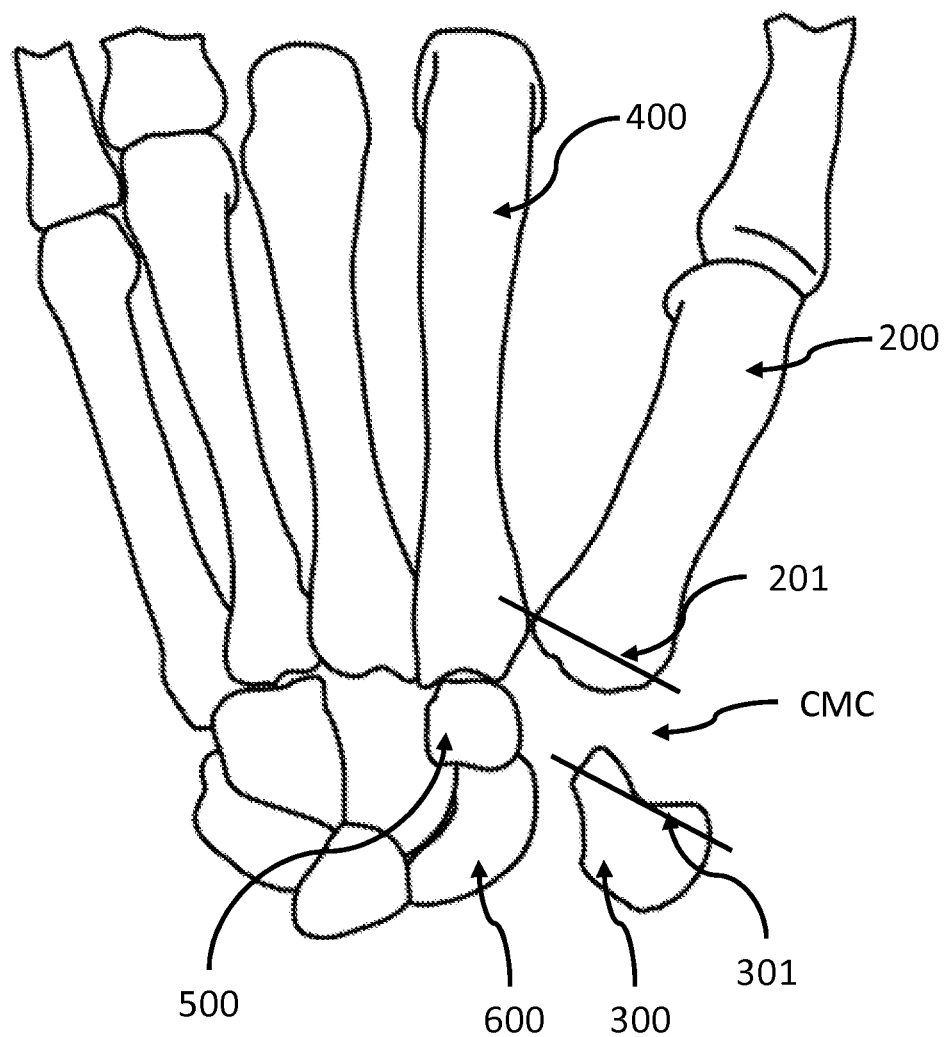
FIG. 2B is a schematic view of the artificial implant for the carpometacarpal joint according to the preferred embodiment of the present invention when cutting and removing a damaged proximal end articular surface of the first metacarpal bone.
FIG. 2C is a schematic view of the artificial implant for the carpometacarpal joint according to the preferred embodiment of the present invention when the artificial implant for the carpometacarpal joint is inserted into the bone marrow cavity of the first metacarpal bone.
FIG. 2D is a schematic view of the artificial implant for the carpometacarpal joint according to the preferred embodiment of the present invention when a suture passes through the suture hole of an attached flange for assisting to fix an abductor pollicis longus to the outer bone surface.

Referring to FIG. 2A to FIG. 2D, in the preferred embodiment of the present invention, the artificial implant 100 for a carpometacarpal joint is applied for arthroplasty surgery, for replacing the damaged carpometacarpal joint. The surgical process comprises steps, as follows:

Referring to FIG. 2A, in a first step, a wound is cut from the skin of the root of the thumb, and a portion of the APL tendon attached to the outer bone surface of the first metacarpal bone 200 is moved aside by a forceps for at least exposing the first metacarpal bone 200 and the trapezium 300. The carpometacarpal (CMC) joint is located between the first metacarpal bone 200 and the trapezium 300. FIG. 2A is an example of a right hand direction, but the surgical process is practically not limited thereto.

Referring to FIG. 2B, in a second step, the joint capsule of the carpometacarpal joint is opened, and a damaged proximal end articular surface of the first metacarpal bone 200 near the carpometacarpal joint is cut and removed to form an incision 201. If it is necessary to replace the proximal end articular surface of the trapezium 300 near the carpometacarpal joint by a corresponding implant, the proximal end articular surface of the trapezium 300 can be also removed at the same time to form another incision 301. Further, FIG. 2B also illustrates the other adjacent bones, such as the second metacarpal bone 400, the trapezoid 500 and the navicular bone 600, so as to facilitate a clear understanding of the relative position of the bones.

Figure 2C:
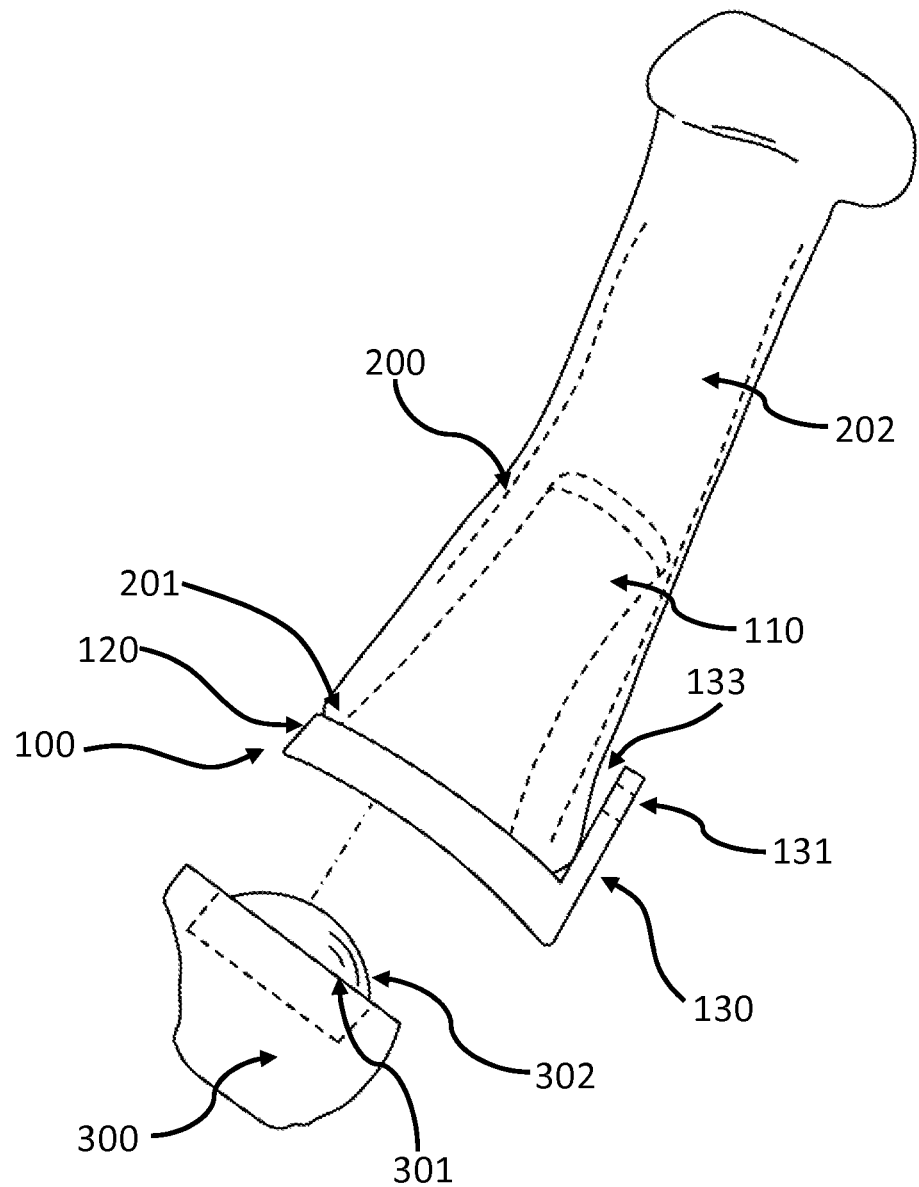

Next, referring to FIG. 2C, it only briefly illustrates the first metacarpal bone 200 and the trapezium 300 of FIG. 2B. In a third step, the artificial implant 100 for the carpometacarpal joint is inserted into the bone marrow cavity 202 of the partially cut first metacarpal bone 200 through the incision 201 thereof in manner of the articular replacement portion 120 facing outward and the insert portion 110 facing inward. It should be noted that, before the artificial implant 100 for the carpometacarpal joint of the present invention is inserted into the bone marrow cavity 202, it is unnecessary to drill any hole on a bone wall of the first metacarpal bone 200 in advance for being used as an attachment for fixing the artificial implant. Thus, the surgical process can be relatively simple. If necessary, the incision 301 of the trapezium 300 is formed in advance, and the other artificial implant 302 also can be embedded into the incision 301.

Figure 2D:
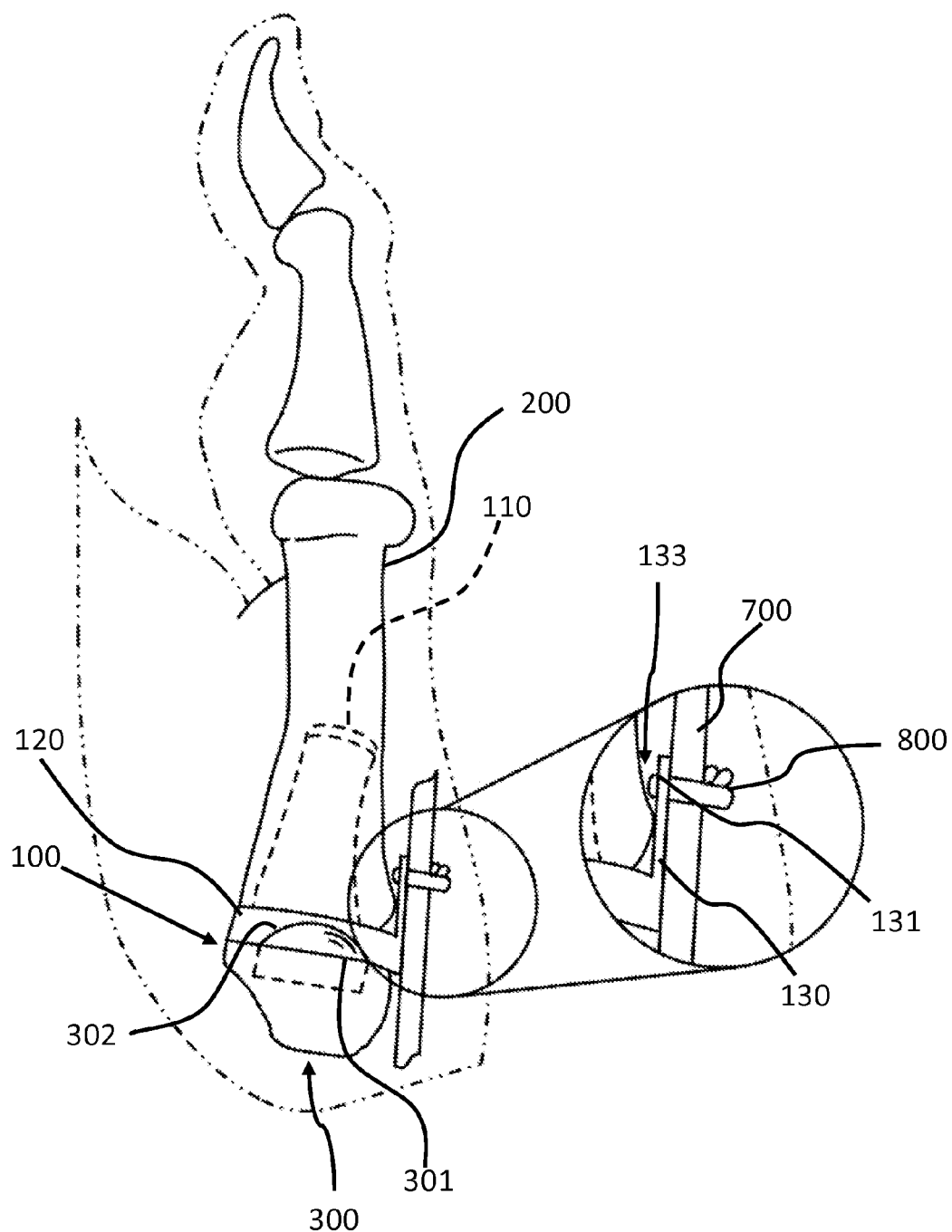

Subsequently, referring to FIG. 2D, in a fourth step, according to the design of the artificial implant 100 of the present invention, the attached flange 130 is preferably located at the radial side of the first metacarpal bone 200. That is to say, the attached flange 130 is located at a position offsetting 1 to 45 degrees toward an outer side of a palm from the intersection point of the peripheral of the articular profile surface 121 for being corresponding to the location of the abductor pollicis longus 700 of the first metacarpal bone 200, wherein an interval 133 is formed between the attached flange 130 and the first metacarpal bone 200 (also as shown in FIG. 2C), and the attached flange 130 is used to allow at least one suture 800 to pass through the interval 133 and the suture hole 131, so that the suture hole 131 provides a structural base for securing the suture 800. In the embodiment of the present invention, the interval 133 formed between the attached flange 130 and the first metacarpal bone 200 is equal to ½ to 5/2 of the thickness of the attached flange 130, such as 0.5, 1, 1.2, 1.25, 1.5, 2 or 2.5 times thereof; the suture 800 is made of biocompatible or biodegradable material and can be a single strand type, a double strand type or a multi-strand type, but not limited thereto.

In suturing, the abductor pollicis longus 700 attached to the outer bone surface of the first metacarpal bone 200 is returned by a forceps, then the suture 800 passes through the suture hole 131 and the interval 133, and is knotted with the abductor pollicis longus 700 by Krackow suturing or other suturing techniques, wherein the attached flange 130 is attached and flush to the outer bone surface of the first metacarpal bone 200 adjacent to the incision 201. Therefore, after the abductor pollicis longus 700 is stitched on the attached flange 130 by at least two sutures 800, it would be beneficial to allow the abductor pollicis longus 700 to be attached and flush to the outer bone surface of a front side of the first metacarpal bone 200 in a manner of surface contact, for the purpose of reattaching the tendon of a abductor pollicis longus to the outer bone surface.

Finally, the wound of the skin is sutured to complete the arthroplasty surgery of the carpometacarpal joint. It should be noted that, during the surgery process, the abductor pollicis longus 700 can be sutured and fixed to the outer bone surface of the first metacarpal bone 200 and the attached flange 130 without cutting the abductor pollicis longus 700, so as to simplify the arthroplasty surgery of the carpometacarpal joint.

As described above, in comparison with the traditional artificial implant for the carpometacarpal joint, it can relieve the pain of the carpometacarpal joint arthritis, but needs to drill holes on the first metacarpal bone or to cut the abductor pollicis longus before implanting the artificial implant, such that the complexity and inconvenience of the arthroplasty surgery is increased. Thus, in contrast, the artificial implant for the carpometacarpal joint of the present invention is provided with the suture hole 131 formed on the attached flange 130 of the artificial implant 100 for the carpometacarpal joint, which not only can omit the step of drilling holes on the first metacarpal bone but also can easily fix the surgical suture on the artificial implant without destroying the abductor pollicis longus. As a result, the present invention can simplify the surgical steps and improve surgical efficiency, thereby increasing the success rate of the arthroplasty surgery of the artificial implant for the carpometacarpal joint.

The present invention has been described with a preferred embodiment thereof and it is understood that many changes and modifications to the described embodiment can be carried out without departing from the scope and the spirit of the invention that is intended to be limited only by the appended claims.

What is claimed is:

1. An artificial implant for a carpometacarpal joint, used for replacing a carpometacarpal joint surface of a first metacarpal bone and comprising:

an insert portion having an inserting end for inserting into a bone marrow cavity exposed from an incision of the first metacarpal bone, and a front end;

an articular replacement portion connected to the front end of the inserting portion and disposed outside the incision of the first metacarpal bone, and having an articular profile surface to replace the carpometacarpal joint surface of the first metacarpal bone; and an attached flange protruded from a peripheral of the articular replacement portion, configured to be attached to an outer bone surface of the first metacarpal bone adjacent to the incision, and having at least one suture hole;

wherein an interval is formed between the attached flange and the first metacarpal bone, and at least one suture passes through the interval and the at least one suture hole, and the at least one suture is knotted with an abductor pollicis longus for assisting to fix the abductor pollicis longus to the outer bone surface;

wherein the articular profile surface of the articular replacement portion is elliptical and includes a major axis and a minor axis, the major axis and the minor axis are crossed at a first intersection point, one end of the major axis close to the attached flange and the peripheral of the articular replacement portion are crossed at a second intersection point, a line is defined from the first intersection point to the attached flange, and an included angle defined between the line and the major axis is 1° to 45°, so that the attached flange is positioned and offset with respect to the second intersection point based on the articular profile surface; and wherein a ratio of the length of the major axis of the articular profile surface of the articular replacement portion and the length of the attached flange is 10:1 to 2:1.

2. The artificial implant for the carpometacarpal joint according to claim 1, wherein the attached flange is integrally connected to the articular replacement portion through a tilting connection surface.

3. The artificial implant for the carpometacarpal joint according to claim 1, wherein the at least one suture hole is circular, oval or regular polygonal.

4. The artificial implant for the carpometacarpal joint according to claim 1, wherein the insert portion, the articular replacement portion and the attached flange are integrated into one piece.

5. The artificial implant for the carpometacarpal joint according to claim 4, wherein material of the insert portion, the articular replacement portion and the attached flange are titanium, silica gel, zirconia or pyrocarbon.

6. The artificial implant for the carpometacarpal joint according to claim 4, wherein the insert portion, the articular replacement portion and the attached flange are made of biocompatible metal or alloy and processed by powder injection molding and high-temperature sintering.

7. The artificial implant for the carpometacarpal joint according to claim 1, wherein the articular profile surface is saddle-shaped, double parabolic concave discoid, single parabolic concave discoid, spherical, hemispherical, polygonal spherical or polygonal hemispherical.

8. The artificial implant for the carpometacarpal joint according to claim 7, wherein material of the insert portion, the articular replacement portion and the attached flange are titanium, silica gel, zirconia or pyrocarbon.

* * * * *